US00PP23866P3

(12) United States Plant Patent
Bradford

(10) Patent No.: US PP23,866 P3
(45) Date of Patent: Sep. 3, 2013

(54) PEACH TREE NAMED 'IVORY MAY'

(50) Latin Name: *Prunus persica*
Varietal Denomination: Ivory May

(76) Inventor: Lowell Glen Bradford, Le Grand, CA (US)

( * ) Notice: Subject to any disclaimer, the term of this patent is extended or adjusted under 35 U.S.C. 154(b) by 119 days.

(21) Appl. No.: 13/374,010

(22) Filed: Dec. 8, 2011

(65) Prior Publication Data

US 2013/0152255 P1 Jun. 13, 2013

(51) Int. Cl.
*A01H 5/00* (2006.01)

(52) U.S. Cl.
USPC ..... Plt./195

(58) Field of Classification Search
USPC ..... Plt./195
See application file for complete search history.

(56) References Cited

U.S. PATENT DOCUMENTS

PP17,282 P2 12/2006 Bradford

*Primary Examiner* — June Hwu

(57) ABSTRACT

The present invention relates to a new and distinct variety of peach tree, *Prunus persica,* broadly characterized by a large size, vigorous, hardy, self-fertile, productive and regular bearing tree. The variety blooms between the early and mid season and requires about 550 chilling hours. The fruit matures under the ecological conditions described in the latter part of May, with first picking on May 20, 2011. The fruit is uniformly medium in size, a balance of acid and sugar in flavor, globose in shape, clingstone in type, firm and melting in texture, white in flesh color, and mostly red in skin color.

1 Drawing Sheet

Botanical classification: *Prunus persica.*
Variety denomination: 'IVORY MAY'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'Ivory May'.

The present variety was hybridized by me in 2003 as a first generation cross using an unnamed white flesh clingstone peach designated by code number '32P462' as the selected seed parent and an unnamed yellow flesh clingstone peach designated by code number '53P100' as the selected pollen parent. The fruit of this cross was gathered that spring, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2006 I selected the present variety as a single tree from the group of seedlings described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '32P462' (unpatented) peach, by producing peaches that are medium in size, clingstone in type, white in flesh color, somewhat acidic in flavor, and mostly red in skin color, but is quite distinguished therefrom by producing fruit that is firmer and that matures about thirty days earlier.

The present variety is similar to its pollen parent, '53P100' (unpatented) peach, by producing peaches that are firm, clingstone in type, and mostly red in skin color, but is distinguished therefrom by producing fruit that is melting instead of non-melting in texture, that is larger in size, and that is white instead of yellow in flesh color.

The present variety is most similar to 'Ivory Duchess' peach (U.S. Plant Pat. No. 17,282) by producing fruit that is white in flesh color, mostly red in skin color, and clingstone in type, but is distinguished therefrom by having reniform instead of globose leaf glands and by producing fruit that is somewhat acidic in flavor instead of sub-acidic, that is smaller in size, and that matures about fifteen days earlier.

SUMMARY OF VARIETY

In summary, the present variety is characterized by a large size, vigorous, hardy, self-fertile, productive and regular bearing tree. The variety blooms between the early and mid season and requires about 550 chilling hours. The fruit matures under the ecological conditions described in the latter part of May, with first picking on May 20, 2011. The fruit is uniformly medium in size, a balance of acid and sugar in flavor, globose in shape, clingstone in type, firm and melting in texture, white in flesh color, and mostly red in skin color.

DRAWING

The accompanying photograph consists of four whole fruits positioned to display the characteristics of the skin color and form, one divided fruit to reveal the flesh and stone, a young tip shoot, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on May 25, 2011, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: '32P462' (unpatented) peach.
Pollen parent: '53P100' (unpatented) peach.

TREE

Size: Large, reaching and maintaining a height of 9' [2.74 m.] and a spread of 7' [2.13 m.] after eight growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase type.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 550 hours.
Trunk:
- *Size.*—Medium, reaching a maximum diameter of 5½" [139.7 mm.] after the eighth growing season.
- *Texture.*—Medium to shaggy.
- *Bark color.*—A Grayish brown [61. gy.Br] and Moderate brown [58. m.Br] variegation with a few Light yellowish brown [76. l.yBr] crevices present.
- *Lenticels.*—Approximate Number Per Square Inch: 6. Color: Light yellowish brown [76. l.yBr]. Average Size: ⅛" [3.2 mm.] to 7⁄16" [11.1 mm.]. Shape: Eye-shaped, elongated.

Branches:
- *Size.*—Diameter of main scaffold is 3¾" [95.3 mm.] measured 12" above the crotch, diameter of limb is 1¼" [31.8 mm.] measured 12" above the first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: A Moderate yellowish brown [77. m.yBr] and Strong yellowish brown [74. s.yBr] variegation.
- Lenticels.—Number Per Square Inch: About 80 on second year wood. Color: Light yellowish brown [76. l.yBr]. Average size: 1⁄64" [0.4 mm.] to 1⁄16" [1.6 mm.] on second year wood. Shape: Eye-shaped, elongated.

Leaves:
- *Size.*—Medium. Average Length: 5½" [139.7 mm.]. Average Width: 1 7⁄16" [36.5 mm.].
- *Arrangement.*—Alternate.
- *Thickness.*—Medium.
- *Form.*—Elliptical.
- *Apex.*—Acuminate.
- *Base.*—Acute, with an average base angle of 50 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Strong yellow green [117. s.YG].
- *Petiole.*—Average Length: ⅜" [9.5 mm.]. Average Thickness: 1⁄16" [1.6 mm.]. Color: Moderate yellow green [120. m.YG].
- *Stipules.*—Number: Usually 2 per leaf, up to 6 per growing tip. Average Length: ¼" [6.4 mm.]. Color: Strong yellow green [117. s.YG] becoming Moderate reddish brown [43. m.rBr] with maturity.
- *Glands.*—Number: 2 to 4 per leaf. Position: Alternately positioned on petiole and base of blade. Size: Medium. Form: Reniform. Color: Light yellow green [119. l.YG] becoming Strong yellow green [117. s.YG] with age.
- *Leaf buds.*—Pointed, medium in size.

Flower buds:
- *Hardiness.*—Hardy, with respect to central California winters.
- *Diameter.*—Typically ⅜" [9.5 mm.] 1 week before bloom.
- *Length.*—Typically 11⁄16" [17.5 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, typically about thirty stamens, five sepal and petal locations alternately positioned.
- *Type.*—Showy, large.
- *Average flower diameter.*—2 3⁄16" [55.6 mm.].
- *Number of petals.*—Usually five, extra petal fragments are occasionally observed.
- *Petal shape.*—Circular to oval.
- *Petal margin.*—Entire, wavy.
- *Average petal diameter.*—¾" [19.1 mm.].
- *Average petal length.*—13⁄16" [20.6 mm.].
- *Petal apex.*—Rounded.
- *Petal base.*—Rounded to somewhat truncate.
- *Petal color.*—Pale pink [7. p.Pk] toward the apex, Light purplish pink [249. l.pPk] toward the base on both sides.
- *Anther color.*—Deep orange [51. deep O] over a Light yellow [86. l.Y] center at bloom onset.
- *Stigma color.*—Light greenish yellow [101. l.gY].
- *Sepal color.*—Dark purplish red [259. d.pR] on the outer surface.
- *Sepal length.*—¼" [6.4 mm.].
- *Sepal width.*—3⁄16" [4.8 mm.].
- *Sepal apex.*—Rounded to elliptical to match the sepal length and width.

*Sepal margin.*—Fairly smooth.
*Average pistil length.*—1 1/16" [17.5 mm.].
*Average stamen length.*—9/16" [14.3 mm.].
*Fragrance.*—Moderate.
*Blooming period.*—Early to medium, three days after 'Ice Princess' (U.S. Plant Pat. No. 12,974) peach.
*Onset of bloom.*—One percent on Feb. 23, 2011.
*Date of full bloom.*—Mar. 6, 2011.
*Duration of bloom.*—One to two weeks, dependent on ambient temperature.
*Number per cluster.*—1 to 3 with single flowers most common.

FRUIT

Maturity when described: Firm ripe, May 25, 2011.
Date of first picking: May 20, 2011.
Date of last picking: Jun. 3, 2011.
Size: Uniform, medium.
*Average diameter axially.*—2 5/8" [66.7 mm.].
*Average diameter across suture plane.*—2 3/4" [69.9 mm.].
*Average diameter across cheek plane.*—2 7/8" [73 mm.].
*Typical weight.*—5.6 ounces [158.7 grams].
Form: Globose, some are slightly asymmetrical.
*Longitudinal section form.*—Round.
*Axial view.*—Round.
Suture: Extends from the base, along the side, to the pistil point.
*Near the base.*—A line in a shallow groove.
*Along the side.*—A line in a shallow trough.
*Near the apex.*—A line in a shallow groove.
Ventral surface: Rounded, lipped toward the base and apex on both sides.
Lips: Unequal.
Cavity: Flaring, elongated in the suture plane, suture showing on one side, Pale yellow green [121. p.YG] stem markings typical.
*Depth.*—5/16" [7.9 mm.].
*Breadth.*—3/4" [19.1 mm.].
Base: Truncate, slightly cordate if viewed parallel the suture plane.
Apex: Rounded, cordate if viewed parallel to the suture plane.
Pistil point: Oblique, very short, depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed.
*Color.*—Dark red [16. d.R] over a Light orange yellow [70. l.OY].
*Down.*—Medium, rolls up when rubbed.
Flesh:
*Color.*—Yellowish white [92. yWhite].
*Surface of pit cavity.*—Covered with Light yellow green [119. l.YG] fibers.
*Amygdalin.*—Moderate.
*Juice.*—Moderate, rich.
*Texture.*—Firm, melting.
*Fibers.*—Fine, tender.
*Ripens.*—Earlier toward the apex.
*Flavor.*—A tasty balance of acid and sugar, typically 12 to 14 brix.
*Aroma.*—Very slight.
*Eating quality.*—Good.

STONE

Type: Clingstone.
Form: Oval.
Hilum: Narrow, oblong.
Base: Straight.
Apex: Acute with an average angle of 60 degrees.
Sides: Equal.
Surface: Irregularly furrowed toward the apex, pitted toward the base.
Ridges: Rounded.
External color: Light yellow green [119. l.YG].
Pit wall color when cracked: Light yellowish brown [76. l.yBr].
Cavity surface color: Pale yellow green [121. p.YG].
Average pit wall thickness: 1/4" [6.4 mm.]
Average width: 3/4" [19.1 mm.].
Average length: 1 3/16" [30.2 mm.].
Average breadth: 5/8" [15.9 mm.].
Tendency to split: Very slight.
Kernel:
*Form.*—Oval.
*Skin color.*—Dark orange yellow [72. d.OY] when first removed.
*Pellicle color.*—Moderate yellowish brown [77. m.yBr].
*Vein color.*—Deep yellowish brown [75. deep yBr].
*Taste.*—Bitter.
*Viable.*—Yes.
*Average width.*—3/8" [9.5 mm.].
*Average length.*—9/16" [14.3 mm.].
*Amygdalin.*—Scant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Ivory Duchess' peach (U.S. Plant Pat. No. 17,282) by producing fruit that is white in flesh color, mostly red in skin color, and clingstone in type, but is distinguished therefrom by having reniform instead of globose leaf glands and by producing fruit that is somewhat acidic in flavor instead of sub-acidic, that is smaller in size, and that matures about fifteen days earlier.

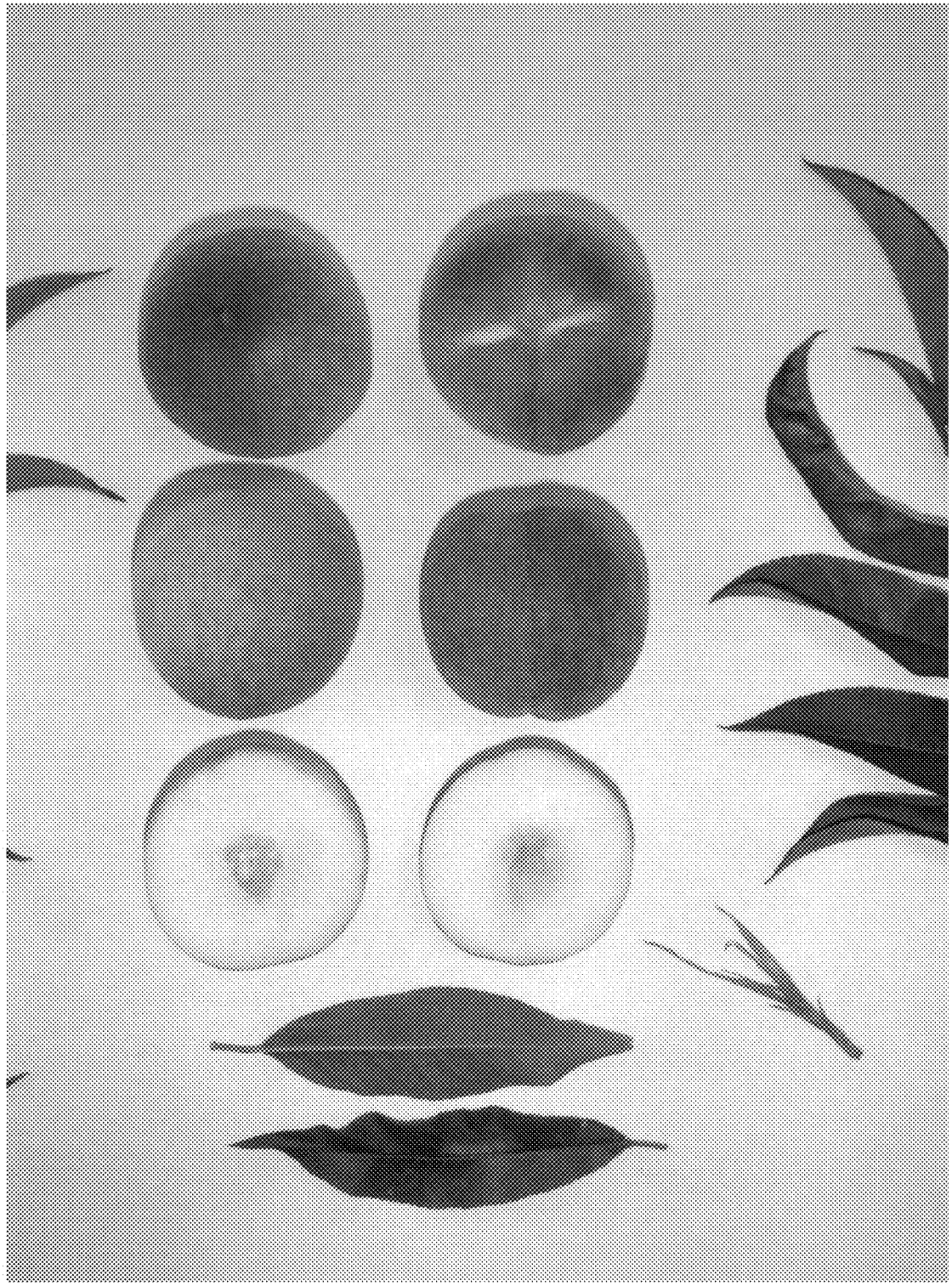

* * * * *